US010555711B2

(12) United States Patent
Wang et al.

(10) Patent No.: US 10,555,711 B2
(45) Date of Patent: Feb. 11, 2020

(54) APPARATUS AND METHOD FOR LOW DOSE MAMMOGRAPHY USING AUGER IMAGER (71) Applicant: NanoX-Medical Corp, Long Island City, NY (US)

(72) Inventors: Chia Gee Wang, Long Island City, NY (US); Zhao Cheng, Woodside, NY (US)

(73) Assignee: NANOX-MEDICAL CORP, Long Island City, NY (US)

(*) Notice: Subject to any disclaimer, the term of this patent is extended or adjusted under 35 U.S.C. 154(b) by 410 days.

(21) Appl. No.: 15/453,274

(22) Filed: Mar. 8, 2017

(65) Prior Publication Data
US 2018/0078229 A1 Mar. 22, 2018

Related U.S. Application Data (60) Provisional application No. 62/395,754, filed on Sep. 16, 2016, provisional application No. 62/468,411, filed on Mar. 8, 2017.

(51) Int. Cl.
A61B 6/00 (2006.01)
(52) U.S. Cl.
CPC ............ A61B 6/502 (2013.01); A61B 6/4233 (2013.01); A61B 6/484 (2013.01)
(58) Field of Classification Search
None
See application file for complete search history.

(56) References Cited

U.S. PATENT DOCUMENTS 4,425,423 A    1/1984  Wang
5,627,871 A *  5/1997  Wang .................. G03F 9/70
                                                378/121
(Continued)

OTHER PUBLICATIONS

R. Ballabriga, et al., "The Medicpix3 Prototype, a Pixel Readout Chip Working in Single Photon Counting Mode With Improved Spectrometric Performance", 2003 IEEE Nuclear Science Symposium Conference Report, pp. 3557-3561.
(Continued)

Primary Examiner — Thomas R Artman
(74) Attorney, Agent, or Firm — Ladas & Parry LLP (57) ABSTRACT An apparatus for low dose mammography including:
(1) a monochromatic X-ray beam generator that emits a first beam of monochromatic line emission X-ray photons having an energy at or nearly above an absorption edge of a first element to induce emission of Auger electrons when the first element is irradiated with the X-ray photons; and
(2) an X-ray detector including
(a) a pixel or plurality of pixels including an array of pixel sensors each of which has (i) a direct conversion layer configured for receiving the X-ray photons and for converting the X-ray photons into a transient electric charge, the direct conversion layer comprising the first element such that the line emission X-ray photons causes a cascade of Auger electrons that form the transient electric charge, and (ii) a semiconductor collection layer configured for receiving Auger electrons of said electric charge from the conversion layer; and
(b) processing electronics for converting the electric charge received in the collection layer into a radiographic signal. Also, a method for using the apparatus for low dose mammography.

13 Claims, 7 Drawing Sheets

(56) References Cited

U.S. PATENT DOCUMENTS

| | | | |
|---|---|---|---|
| 7,180,981 B2 | 2/2007 | Wang | |
| 7,430,276 B2 | 9/2008 | Wang et al. | |
| 7,649,981 B2 * | 1/2010 | Seppi | A61B 6/032 378/124 |
| 7,869,862 B2 * | 1/2011 | Seppi | A61B 6/032 600/420 |
| 8,311,185 B2 * | 11/2012 | Seppi | A61B 6/032 378/111 |
| 8,406,378 B2 * | 3/2013 | Wang | H01J 35/08 378/121 |
| 8,680,474 B2 | 3/2014 | Soh et al. | |
| 9,476,991 B2 * | 10/2016 | Vora | G01T 1/2018 |
| 9,588,235 B2 | 3/2017 | Weisfield et al. | |
| 2004/0042585 A1 | 3/2004 | Nagarkar | |
| 2005/0082491 A1 * | 4/2005 | Seppi | A61B 6/032 250/370.11 |
| 2005/0084060 A1 * | 4/2005 | Seppi | A61B 6/032 378/5 |
| 2005/0084073 A1 * | 4/2005 | Seppi | A61B 6/032 378/156 |
| 2005/0123097 A1 * | 6/2005 | Wang | H01J 35/08 378/143 |
| 2005/0185756 A1 * | 8/2005 | Wang | A61B 6/502 378/37 |
| 2010/0111388 A1 * | 5/2010 | Seppi | A61B 6/032 382/130 |
| 2011/0133094 A1 * | 6/2011 | Seppi | A61B 6/032 250/367 |
| 2012/0051496 A1 * | 3/2012 | Wang | H01J 35/08 378/4 |
| 2015/0139390 A1 | 5/2015 | Bellazzini | |
| 2016/0097864 A1 * | 4/2016 | Vora | G01T 1/2018 257/428 |
| 2018/0078229 A1 * | 3/2018 | Wang | A61B 6/502 |

OTHER PUBLICATIONS

Auweter, S.D., et al. X-ray phase-contrast imaging of the breast—advances towards clinical implementaion. Br J Radiol. Feb. 2014; 87/1034) Jun. 6, 2013.

* cited by examiner

Coolidge X-ray beam with wide Fan beam angles parallel to the target surface of a rotating anode disk

APPARATUS AND METHOD FOR LOW DOSE MAMMOGRAPHY USING AUGER IMAGER

CROSS REFERENCE TO RELATED APPLICATION

This application claims priority from U.S. Provisional Patent Application Ser. Nos. 62/395,754, filed 16 Sep. 2016 and 62/468,411 filed Mar. 8, 2017, and incorporates herein by reference the entire contents of both applications.

FIELD OF THE INVENTION

The invention is directed to an apparatus comprising an X-ray generator that emits monochromatic line emission X-ray photons so that the X-ray photons are transmitted through the tissue of a subject to a sensor/detector that can detect a phase shift in the X-ray photons after they pass through the tissue. The invention is also directed to a method for detecting an abnormality in the tissue using the apparatus.

BACKGROUND OF THE INVENTION

One in eight women may develop breast cancer in her life time, and mammography has largely been credited for the early detection of breast cancer that leads to an early therapy and a five year survival rate of well beyond 90%.

Although, as discussed below, more advanced digital technologies have been developed to improve mammography image quality, there are three limitations associated with mammography that call for improvements. First, mammograms miss up to 20% of breast cancers that are present as false negative. Second, in some cases a mammogram appears abnormal, yet there is no breast cancer, thus result in a false positive. Third, the risk of radiation induced carcinoma for woman in general before age 50 due to the statistics that mammography may not gain sufficient benefit from its use. Also most patients complain on the procedure of breast compression.

In more practical considerations of instrument design, soft tissues have very weak shadow contrast from X-ray attenuation contrast (XAC), and mammography allows only ~5% of the X-ray beam to reach the detector while 95% of fluence is absorbed by the compressed breast in order to deliver a useful shadow image from a weak XAC. This XAC approach limits the beam energy for mammography at 14±3 keV, which can be delivered by a Coolidge tube using a rotating anode at a tube bias of 24±4 kVp. The anode metal is coated with Rh in order to avoid any line-emission which cannot be part of the variable of bias necessary to adjust for a range of tissue thickness and density. Also because of the interference to the imager from wide-angled Compton scattering, the use of moving Bucky grid with a narrow cone beam angle to cover the breast restricted the minimal length of X-ray beam path to be long and the instrument less efficient. Thermal load of the mammo-tube at 4.5-6.5 kW implies the use of a rotating anode to spread the heat from an e-beam focal point.

Some of the digital advancements alluded to above are described in US Patent Application Publication 2015/0139390 to Bellazzini (the contents of which are incorporated herein by reference). For example, Bellazzini describes the use of digital X-ray sensors comprising a conversion layer in the form of an amorphous coating, normally made of Amorphous Selenium or of Cesium iodide, and an integration panel, i.e. a collection layer, that has a TFT pixel structure (Thin Film Transistor). The conversion layer serves for transforming into an electric charge the photons of an X-ray beam that has travelled across an irradiated sample. This may occur directly or indirectly, as in the case of amorphous Selenium and of Cesium iodide; respectively. The total charge obtained by the conversion during an X-ray exposure builds up in the pixels of the integration panel. Once the exposure has been completed, the amount of charge accumulated in each pixel is read. More in detail, an image acquisition electronics is provided that comprises an analog-to-digital converter arranged at the boundary of the integration panel (or at a second chip to be stacked beneath the sensor chip). The analog-to-digital converter changes the overall charge accumulated in each pixel into an electric voltage, i.e. into a number that is proportional to the overall radiation that has travelled across the sample at each pixel of the integration panel. These numbers can be converted into a radiographic image in which the contrast depends upon the overall radiation that is accumulated in each pixel.

Bellazzini also describes a so-called "photon-counting" technique that is also described, for example, in U.S. Pat. No. 8,680,474 to Soh, et al (the contents of which are incorporated herein by reference). Using a photon-counting technique, photons can be counted one-by-one, and ranked into a plurality of channels, thus obtaining a "film grade" resolution, i.e. a resolution that is comparable with the resolution allowed by high-resolution radiographic plates. In particular, hybrid detectors exist that are known as Medipix and that are provided with an ASIC for carrying out a photon-counting procedure. These hybrid detectors comprise discriminators associated with event counters that are used in such a way that the image acquisition electronics counts only events, i.e. acquisitions of photons that fall in a predetermined energy window. This way, an X-ray imaging technique is obtained that has spectroscopic features. A more recent device, known as Medipix-3, has a finer energy resolution thanks to a real-time charge share correction. Medipix-3 also comprises multiple pixel counters that can be used in different operation modes. This allows a continuous detection, and up to eight energy thresholds can be obtained.

In the Medipix device, like in other devices, the collection layer is implemented by CMOS technology, which is a low-power consumption device, i.e. about a few Watts, that can be fabricated at a low-cost. As has been developed for optical imagers, the CMOS imagers need to be compared with film resolution at 60 line-pairs per millimeter (lp/mm). A large number of pixels per chip, e.g. about $10^7$, is required for a CMOS imager to compare with x-ray films. For a radiological digital panel with much larger pixel sizes the resolution is only approximately 6 lp/mm.

Notwithstanding these digital manipulations, there is still an urgent need for an apparatus and method that enables enhanced intrinsic resolution mammography and provides improvements over the x-ray attenuation contrast (XAC) imaging discussed above.

SUMMARY OF THE INVENTION

In accordance with a first aspect of the invention, there is provided an apparatus for examining tissue of a patient for abnormalities, the apparatus comprising:
  (1) a monochromatic X-ray beam generator that emits at least a first beam of monochromatic line emission X-ray photons having an energy at or nearly above an absorption edge of a first element to induce emission of Auger electrons when the first element is irradiated with the X-ray photons; and (2) an X-ray detector comprising (a) a pixel or plurality of pixels comprising (i) an array of pixel sensors each of which comprises the first element such that the line emission X-ray photons, when received by the pixel sensors in the array, cause a cascade of Auger electrons that form a transient electric charge, and (ii) a semiconductor collection layer configured for receiving the Auger electrons of said transient electric charge; and (b) processing electronics for converting the Auger electrons received in the collection layer into a direct radiographic signal;

wherein X-ray photons in the first beam of monochromatic line emission X-ray photons undergo a spatial and temporal dispersion when passing through soft tissues with density variation so as to cause a density-based phase shift in the X-ray photons, and wherein the pixel sensors in the array are of a size and number that enable the pixel sensors to register a phase shift contrast (PSC) image from the radiographic signal from which abnormalities in the tissues are identifiable.

In accordance with a preferred embodiment, the monochromatic X-ray beam generator comprises an end window X-ray tube having an evacuated housing that is sealed from the ambient, an end window anode disposed in the housing comprising a transmission target layer, a cathode disposed in the housing which emits an electron beam that proceeds along a beam path in said housing to strike the anode in a spot so as to generate the first beam of monochromatic X-rays which exits the housing through the end window. In accordance with another preferred embodiment, the apparatus comprises a high voltage power supply. In accordance with yet another embodiment, the transmission target layer comprises Sb or La, and the first element is selected from the group consisting of Ag, I and AgI or Cs, I and CsI respectively. In a most preferred embodiment, the target layer comprises La and the first element is CsI, and the K-edge of Cs is induced by the $K_\beta$ emissions of La, while the K-edge of I is induced by the $K_\alpha$ emissions of La.

In accordance with still other preferred embodiments, the pixel sensors in the array of pixel sensors are between 0.1 and 0.2 µm in size, and each pixel comprises the first level of processing electronics covered by a layer of a heavy element to protect the electronics from the X-ray radiation damage, and the array of pixel sensors is on a first semiconductor chip and image manipulating electronics are on a second semiconductor chip that is placed at an edge of the imager panel or stacked beneath the first semiconductor chip to shield the second semiconductor chip from radiation.

In accordance with a second aspect of the invention, there is provided a method for examining breast tissue of a subject for abnormalities, the method comprising the steps of (a) providing the apparatus described above;

(b) emitting from the monochromatic X-ray beam generator at least the first beam of monochromatic line emission X-ray photons so that the X-ray photons are transmitted through the breast tissue and detected by the detector; and (c) causing the detector to generate a radiographic image that reflects a phase shift contrast in the X-ray photons caused by a density variation, including an abnormality in the breast tissue. In a preferred embodiment, the monochromatic X-ray beam generator comprises an end window X-ray tube having an evacuated housing that is sealed from the ambient, an end window anode disposed in the housing comprising a transmission target layer, a cathode disposed in the housing which emits an electron beam that proceeds along a beam path in said housing to strike the anode in a spot so as to generate the first beam of monochromatic X-rays which exits the housing through the end window.

In another preferred embodiment, the examination of the breast tissue is conducted in a manner that enables ≥50% of penetrating X-rays of the first beam to reach the detector after passing through the breast tissue. Preferably, the examination is carried out with an X-ray photon energy of 25 to 35 keV.

In yet another preferred embodiment, with the end window of the tube disposed within about 10 to 15 cm of a breast of the subject and with the first beam focused under 40 µm, a brightness of the end window X-ray tube is adjustable to enable the end window X-ray tube to operate at a thermal load of 100-150 watts for the examination.

DETAILED DESCRIPTION

The invention provides for Phase Shift Contrast (PSC) imaging of tissue, including breast tissue, to provide for low dose mammography of a patient with a number of advantages:

A simple monochromatic X-ray beam generator to produce the necessary PSC instead of x-ray attenuation contrast (XAC).

A higher energy X-ray beam to reach the detector with ≥50% of the X-ray fluence.

A broad-angled uniform X-ray cone beam and a corresponding Auger detector with a direct, discriminating energy window that can lead to a short source/detector distance to form a compact, low cost instrument.

A versatile Auger imager to allow a variable imaging pixel size whose PSC sensor size can be arranged in an array at submicron sensor size in order to satisfy the physics of PSC imaging while display at the conventional 10-200 micron pixels and zoom to single cell dimension for detailed evaluations.

Dose to the breast tissue and the thermal load of the X-ray tube can be reduced by one to two orders of magnitude when coupled with a sharp beam focal point to result with a very compact, low cost, high resolution instrument.

The Auger mammography uses a transmission X-ray tube to provide a largely monochromatic fluorescent line X-ray emission with line width at ~10 eV (Krause, M O and Oliver, J H. "Natural Widths of Atomic K and L levels, Kα x-ray lines and Several KLL Auger Lines" J. Phys. Ref Data, 8 (2): 1979), and broad-angled uniform cone beam. A suitable transmission X-ray tube and method of use are described in U.S. Pat. Nos. 4,425,423, 7,180,981 and 7,430,276, the contents of which are incorporated herein by reference.

In the present invention, the beam of the transmission X-ray tube couples with an Auger sensor imager modified from CMOS optical imager chip whose metal of MOS sensor is replaced by an Auger sensor array with a discriminating energy window for PSC imaging. The efficiency of line-emissions coupled with the Auger sensor enhances the XAC by two or more orders of magnitude, thus allowing a higher X-ray beam energy and reduced source/imager distance to consequently reduce the tissue dose by ~200 fold, or 60 fold without breast compression, and the thermal load of the mammo-tube from 6.5 kW to under one hundred fifty Watts, which also facilitates the X-ray beam to be delivered from a much sharper e-beam focal point useful for PSC imaging. The above mentioned parameters have been combined from several key considerations that are described in separate sections below, namely the High Energy PSC Imaging with High Resolution Auger Imager, the High Efficiency Transmission X-ray Tube, the Simplified High Voltage Power Supply, and the resultant Compact Instrument without using Bucky Grid.

High Energy Phase Shift Contrast Imaging

Phase contrast makes use of coherent photon interference in the E-vector of monochromatic X-rays as they will undergo a slight difference in photon speed when passing through medium with slight change of their indexes of refraction. This interfered photon intensity $\sim|E|^2$ could generate a contrast level PSC at several orders of magnitude higher than those with XAC, and they carry with them a spatial dispersion as well as a temporal dispersion.

Figure 1:
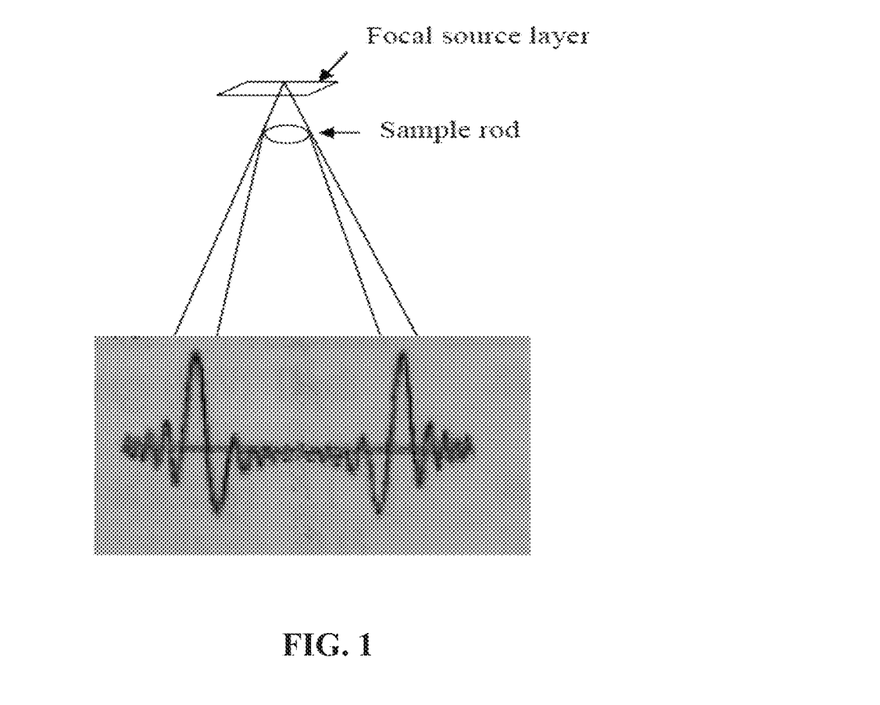
FIG. 1 shows the E-vector in PSC for the edge interfered pattern of a rod from the penumbra attributed from the finite target layer dimensions.

FIG. 1 shows the E-vector in PSC for the edge interfered pattern of a rod. For photon wavelength≥atomic size, or E≤10 keV, edges of the rod will bring the polychromatic wave interfered pattern as shown. And for photon wavelength ≤atomic size, such as the high energy PSC under consideration, the interfered photon waves are attributed largely from the finite size of the X-ray focal spot, or the penumbral of the 40 μm focal spot as estimated in the spatial dispersion δsk.

For PSC practice, the imaging sensor must have an appropriate size in order to register the interfered E-vector amplitude of the monochromatic photon wave front using the K-absorption edge of Ag at 25.5 keV as the example for Auger sensor energy to be excited by the K-lines of Sb at 26.274 keV. This interference have a spatial dispersion δs and a temporal dispersion δt, with $$\delta s \sim \lambda d/p = (1.24 \ \mu m/26,274)(3\times10^5/40) = 0.354 \ \mu m$$

where $\lambda$ is the $k_\alpha$ lines of Sb, d the source/detector distance at 30 cm, and p the focal point at 40 μm; for La $k_\alpha$ lines at ~33 KeV, δs~8.25 μm; and $$\delta t \sim \lambda E/\Delta E = 0.138 \ \mu m$$

where E is the photon energy and δE the line width at ~9 eV for Ag [1]

From the values of δs and δt, the Auger sensor size of 0.1 μm will suffice to register the interfered $E^2$ amplitude of PSC.

High Resolution Auger Imager

The Auger sensors described herein take advantage of the Auger effect wherein, when an atom is probed by a photon or a beam of electrons with energies in the range of several eV to 50 keV, a core state electron can be removed leaving behind a charged atom with a hole. As this is an unstable state, the core hole will be filled by another electron but the atom will have what is described herein as a "transient charge".

Figure 2:
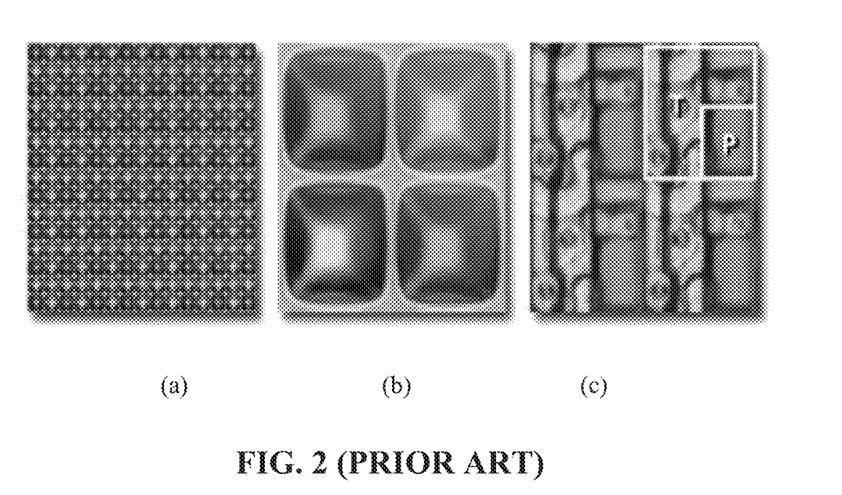
FIGS. 2a-c show conventional a) Imaging Pixel Arrays; b) The 4 pixels as one color filtered unit with one red filter, one blue and two green filters as green being more needed sensitivity to the eyes; and c) The pixel with photodetector P and transistor T and first stage circuit.

In a typical optical image chip with sensor area shown in FIG. 2a, b and c that could be modified for Auger sensors to register the PSC imaging, the area of pixel sensor arrays is surrounded by the first stage of imaging processing circuit followed by, for example, the pixel array shift registers for the read out in x and y directions, parallel analog output amplifiers, and column amplifiers that correct for the fixed pattern noise caused by threshold voltage non-uniformities. The proportion of the sensor area over the chip area is generally called the "Fill Factor", which could vary from 30-90%.

For a single imager chip, the Fill Factor, the input/output contact area is both outside the area of sensor pixels and is of little concern to the imaging sensor. To modify these imager chips for Auger mammography imager, however, many units of these low cost chips must be linked together with large gaps of the non-functional area to form imaging gaps. One solution to form a large integrated sensor area is to place most non-sensor functions such as the input/output area on the back of the sensor chip, and place the processing electronics on a separate chip stacked beneath the sensor chip in order to combine the sensor chips into a large panel without imaging gap. Another advantage of this stacked approach is that the higher energy X-ray beam for Auger mammography has very limited penetration depth in silicon, so that the sensor chip also functions as a radiation shield for the processing chip beneath.

By increasing the mammographic X-ray energy from 14 keV to 26 keV, it enables the more penetrating X-rays to reach the detector with ≥50% of the beam fraction instead of only the left over 5% from the compressed breast tissue. Assuming no change in the photo detector efficiency, then the X-ray beam brightness can be correspondingly reduced by an order of magnitude without altering the detector count, and the corresponding tissue dose is reduced by 10(95/50) =19.

Also by using a transmission X-ray tube shown below, the cone beam emission profile has a uniform output over a broad angle of 170° so that the X-ray focal point can be placed much nearer to the breast and the imager and by avoiding the use of moving Bucky grid because of the discriminating energy window against broad angled Compton scatterings of the Auger sensor so that the Auger imager can be placed much nearer to the breast, thus reducing source/detector distance by a factor of 3, and further reduces the tube brightness need by another order of magnitude. These reductions bring the mammo-tube from the conventional 6.5 kW (or 4.5 kW in Japan) to 100-150 watts, for which the spread of thermal load over a rotating anode surface is no longer necessary. Using a stationary transmission anode target under 150 W, it could easily have the e-beam to be focused under 40 μm without active thermal management.

The Auger imaging sensor will be modified from the CMOS optical imager chip where an array of sub-micron Auger sensor such as an array of Ag (or I or AgI) film of 0.1 μm are deposited as Auger sensor on the oxide as the metal oxide silicon (MOS) to function as the photodetector metal, instead of using the colored optical filter under a micro-lens. This modification is similar to the modification for infrared sensors by replacing color filters with IR filters for IR cameras. In addition, the remaining pixel area where the first stage of CMOS electronics is placed can be covered by a layer of heavy elements such as Ba or Ta in order to protect the CMOS circuit elements from the X-ray radiation.

As an example, the modifications for Auger-based array of photodetector could be an Ag (or I or AgI) coating at the submicron area. (FIG. 2b) with the pixel remaining area (2c) to be covered by a layer of heavy element coated for for protection against X-ray radiation. The coated Auger sensor array points must be unconnected electrically in order to harvest the PSC imaging effect at the 0.1 u level, although the photodetector area could be much larger than the Auger sensor point. Monochromatic X-ray photons could induce inner shell ionization and produce Auger electrons, whose number depends on the Auger yield as against the fluorescent yield. High Z elements have more electrons but much lower Auger yield. Take the K-capture of radioactive iodine as an example, I-125 would give 20 Augers, but I-123 only 10 Augers due to its higher decay energy thus a reduced L/K transition rate. Ag (47) has lower Z than I (53) and thus higher Auger yield, and the Sb K-lines for the K-edge of Ag to yield 15 Augers per inner shell ionization is reasonable.

Figure 9:
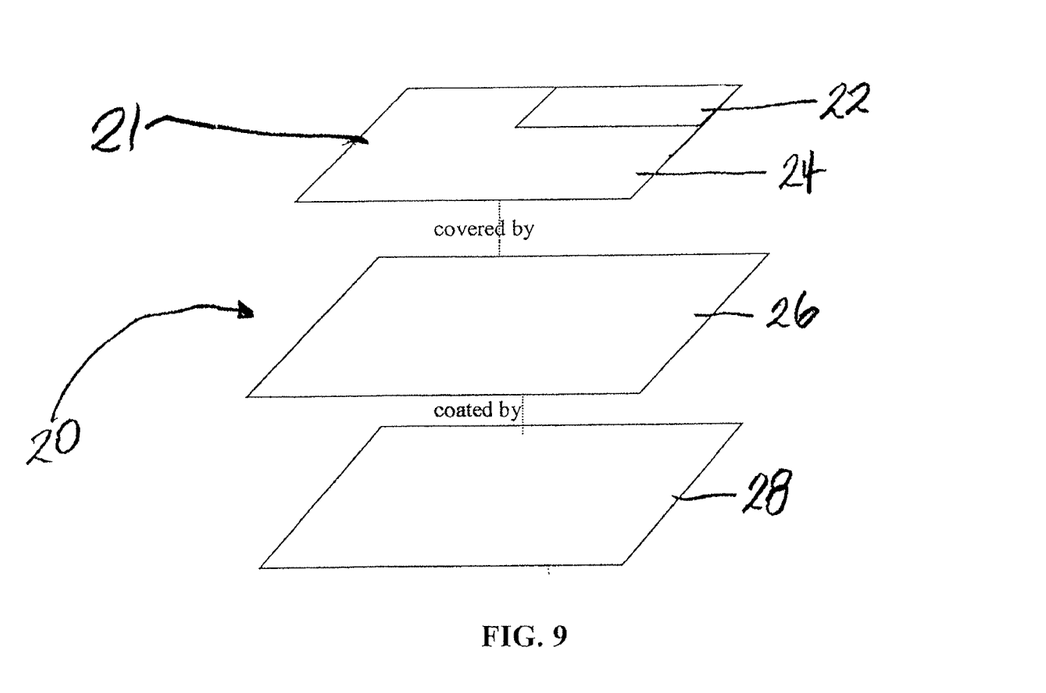
FIG. 9 shows a layout of an Augur imager according to the invention in a preferred embodiment.

The Auger imaging sensor can use exactly the same logic as in a conventional optical CMOS imager. The layout of an Auger imager 20 in a preferred embodiment in shown in FIG. 9, wherein a first layer 21 comprises a metal-oxide-semiconductor (MOS) photodiode 22 and a first stage complementary metal-oxide-semiconductor (CMOS) imaging circuit 24 covered by a second layer 26 comprising a conductive layer, such as Al, to reach the MOS photodiode or a conductive and protective layer, comprising for example Ta, to shield the X-rays and reach the MOS photodiode. The second layer 26 is coated by a third layer 28 comprising an Auger sensor as described herein.

Figure 3:
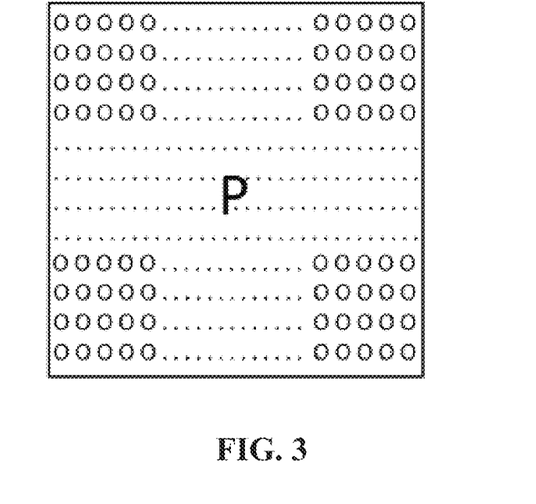
FIG. 3 shows the optical detector P in FIG. 2c modified into an array of Auger sensor detectors at unconnected dots of 0.1 u each deposited on the oxide of a metal oxide semiconductor (MOS) sensor detector.

FIG. 3 shows an array of Auger sensor detectors at unconnected dots of 0.1 u each deposited on the oxide. Note that the Auger sensor size can be made very small or the four pixels in 2 (b) can be connected together to form a larger pixel for display.

In a typical X-ray imager of 20 cm×30 cm, if it is filled with Auger sensor pixels of 1.6 μm each, the number of pixels will reach 23.4 billion, too large a number to be manipulated together. It can be stored in cloud computing for processing and display or the number could be reduced by ~$10^3$ without using the cloud. Let the PSC Auger pixels be grouped in 30×30=900 pixels per each point of display at 50 μm in the imager panel so that it could become approximately the output of a conventional X-ray imager, then the PSC Auger panel could have an almost conventional mammogram viewing as well as an optional zoomed detailed display, showing the thousand fold enhancement in the μm-sized resolution that could indicate the presence of neovasculature, or cyst, at the resolution of single cells without biopsy, for example.

Image Resolution

For photographic films, Kodak and Fuji have commercialized 0.5 μm AgI semi-crystal sheets that are at the photon wave length of visible light and 0.5 μm pieces would provide the optimal scattering cross section with light. Including the use of color filters, the resolution of various color films on the average could resolve about 60 line-pairs/mm. Without color, the high density black and white film could reach a resolution of about 100 line-pairs/mm.

The highest x-ray film image resolution has been the mammogram at about 15 line-pairs per mm. But a 2D image cannot readily be manipulated for easy viewing. A good mammogram would show tubular tissues, fats, blood vessels, etc., but it would require an M.D. mammographer to see all the structure in the mammogram. It is still difficult to get all structure in the mammogram to make physiological sense and to identify extra points like cysts, tumor growths, etc., with false positive and false negative rate often reaching double digits.

Digital mammogram helps greatly for the mammographer to manipulate the image and reduce the false positive and false negative rates even though its image resolution is less than half of that of the films. The more recent 3D digital mammogram is an advance to help mammographers to do a better job without seeing only the compressed, distorted image. Using phase shift contrast (PSC) as in the present invention, the breast tissue need not be compressed as it can be irradiated with far more penetrating, higher energy x-rays with greatly reduced dose.

At high energy, if the breast absorbs only 50% of the fluence, then a 2% density difference between tissues would give XAC only a contrast between 50 or 49 at the detector, i.e., no useful image contrast. With PSC, the contrast level can be higher than XAC by $10^3$-$10^4$. Since the wavelength of high energy photons is very small, one would preferably use an Auger sensor of very small size to register the PSC, e.g., less than 2 μm, preferably, between 0.1 and 2 μm, and most preferably about 0.1 μm. Since, if each pixel is 0.1 μm, the mammogram would be extremely large, the apparatus of the invention can also use a more conventional "pixel" size of, for example, about 200 μm for a more conventional viewing display without breast compression, and allow the mammographer to zoom in on a suspected position for higher, amplified details using smaller pixels of about 0.1 μm. With the smaller pixels, one can reach the level of detail of a single cell as the Auger sensor at 0.1 μm is even smaller than the AgI crystals of classical films used by pathologists to study a biopsy under a microscope.

To estimate a desired size of the Auger sensors of the invention, one can use a "pernumbral", as next explained. The inventor has measured the size of x-ray focal point by placing a mm-sized metal ball in front of the focal point and obtained a 10 inch-sized round image. By measuring the edge of the imaged ball with a densitometer, the size of the image edge can be correlated to the x-ray focal size as well as the focal shape (round or oval). For the apparatus of the invention, the same pernumbral may be used to estimate the desired Auger sensor size with a particular x-ray photon wavelength leading to a sensor spot, for example, that is no larger than 0.2 μm and is preferably about 0.1 μm. With sensors of this dimension, a 20 μm pixel will contain 200×200=40,000 Auger sensors. An enlarged image pixel at 20 μm which contains 40,000 sensors would cover a single cell at about 10 µm. With PSC imaging, it would be possible for a pathologist to forego the study of biopsy samples and instead simply have a mammographer "zoom" a mammogram on a suspected tissue area.

High Efficiency Transmission X-Ray Tube

Figure 4:
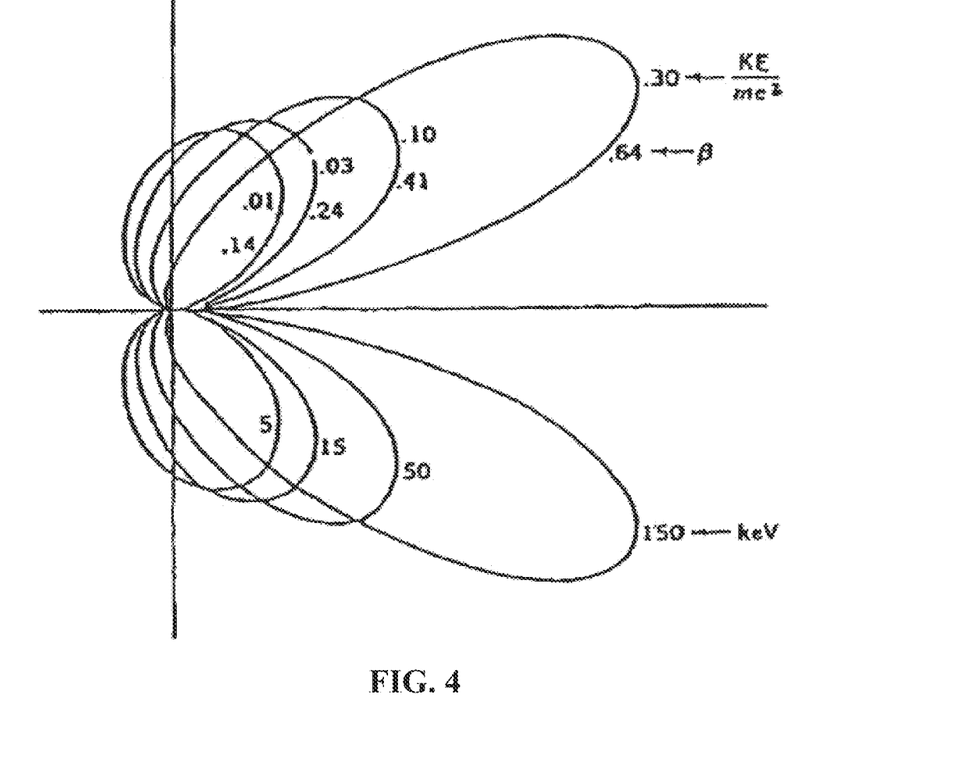
FIG. 4 shows Bremstrahlung Dipole Trajectories Under Relativistic Transform, Moving From 90° of the e-beam Path to Lean Forward and Become Parallel to the e-beam Path.

Being six years older than Einstein, Coolidge of GE designed his X-ray tube over a century ago without engaging relativistic electron dynamics. At one hundred volts, electrons already reach 2% the speed of light, therefore most e-beams in an X-ray tube undergoing bremstrahlung (or brem, the slow down radiation) is really quite relativistic where the brem's dipole trajectory moves from 90° of the e-beam path to become parallel to the e-beam (FIG. 4).

Figure 5:
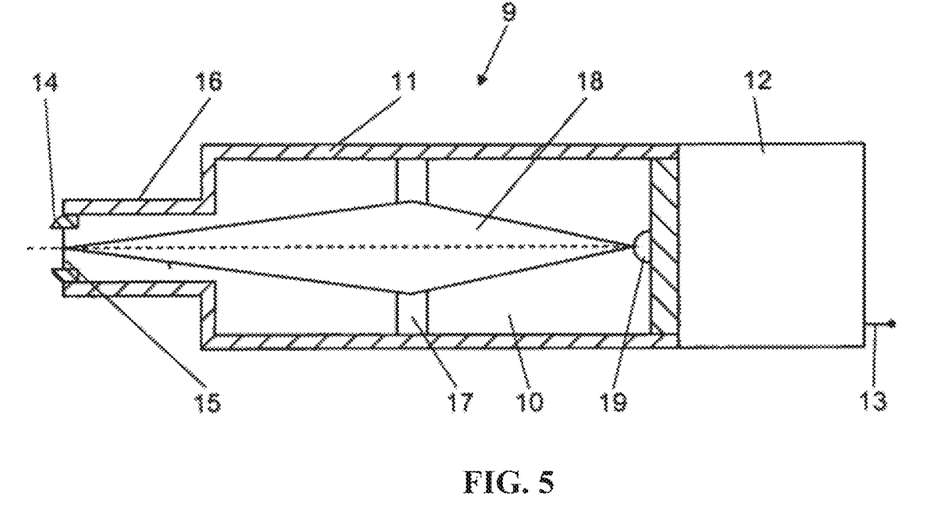
FIG. 5 shows the e-beam in a transmission x-ray tube.

FIG. 5 shows a transmission X-ray tube (9), with vacuum (10), insulating enclosure (11), thermal management (12), anode ground (13), HV negative contact (14), LED induced e-beam source (15), cathode assemble (16), e-beam lens (17), e-beam focal line (18), and transmission anode target/filter (19).

Figure 6A:
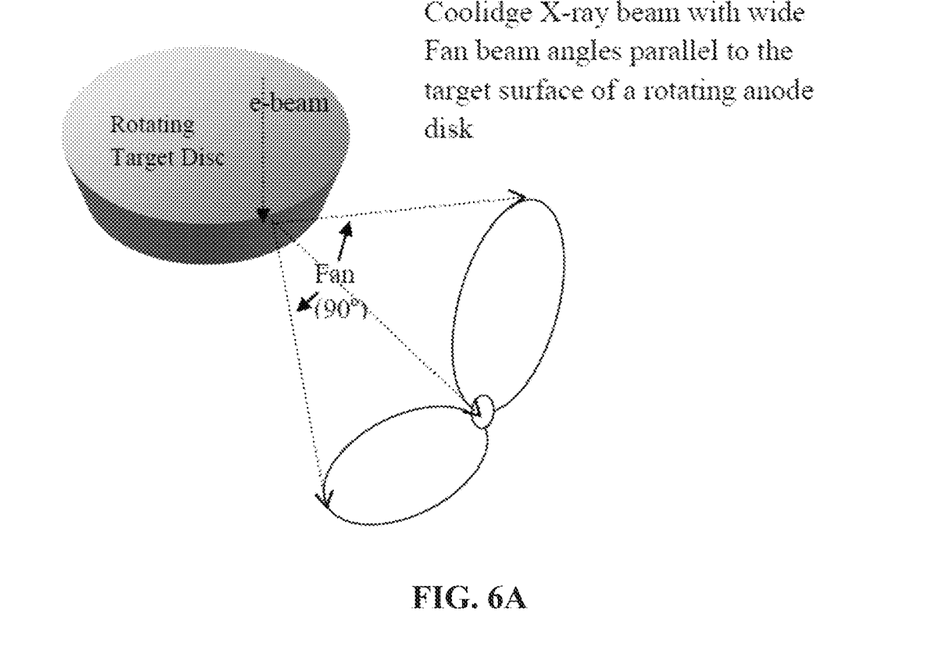
FIGS. 6a and 6b show Coolidge Brem X-ray Fan Beam and Transmission X-ray broad-angled uniform Cone Beam Trajectories respectively.
Figure 6B:
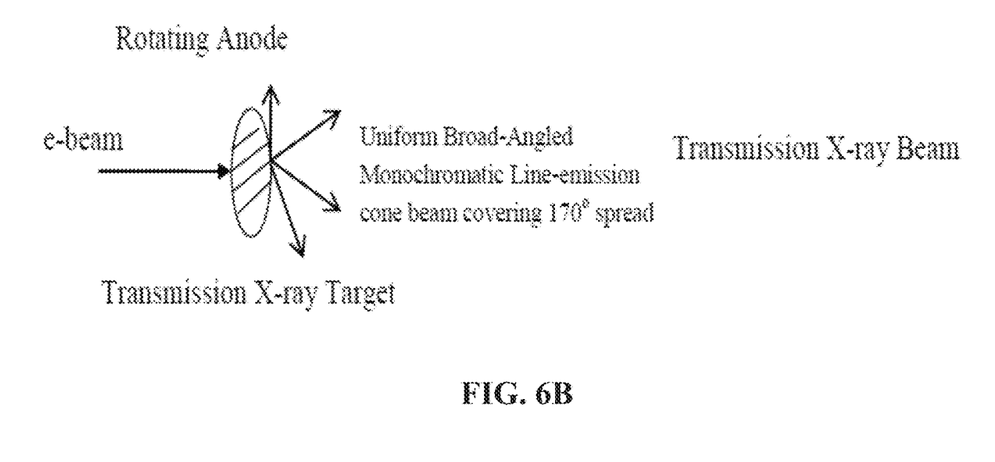

FIG. 6a shows a Coolidge X-ray beam with wide fan beam angles parallel to the target surface of a rotating anode disk. FIG. 6b shows a uniform broad-angled monochromatic line emission cone beam covering 170° spread. FIG. 8 shows transmission tube brightness, mostly in line-emissions, increases with kVp follows the power relationship of $(kVp)^{2.1}$ due to the relativistic transform while the Coolidge tube harvesting the beam at 90° increases to $(kVp)^{1.7}$ While nearly all medical X-ray tubes follow the century old Coolidge patents of GE, the transmission X-ray tube as described with respect to FIGS. 5-8 gain the following advantages:

By combining the filter and fluorescent functions with the target transmission layer to result with a monochromatic line-emissions with fluorescent line width ~10 eV [1].

In a typical 100 kV tube, the uniform broad angled cone beam integrating from all the azimuth angles is brighter than the narrow angled Coolidge beam by 200-300 times.

Characteristic line-emissions are not altered by higher-kVp that gives a higher efficiency by having brightness $\sim(kVp)^{2.1}$.

Making use of the dramatically higher efficiency, the thermal management as well as the high voltage power supply could be much simplified.

For the Auger electrons useful in diagnostic X-ray imaging as well as in MGy dose therapy in Situ, the line-emission of Sb centers for K-edge of silver at 26 keV to generate ~15 Auger electrons.

Figure 7A:
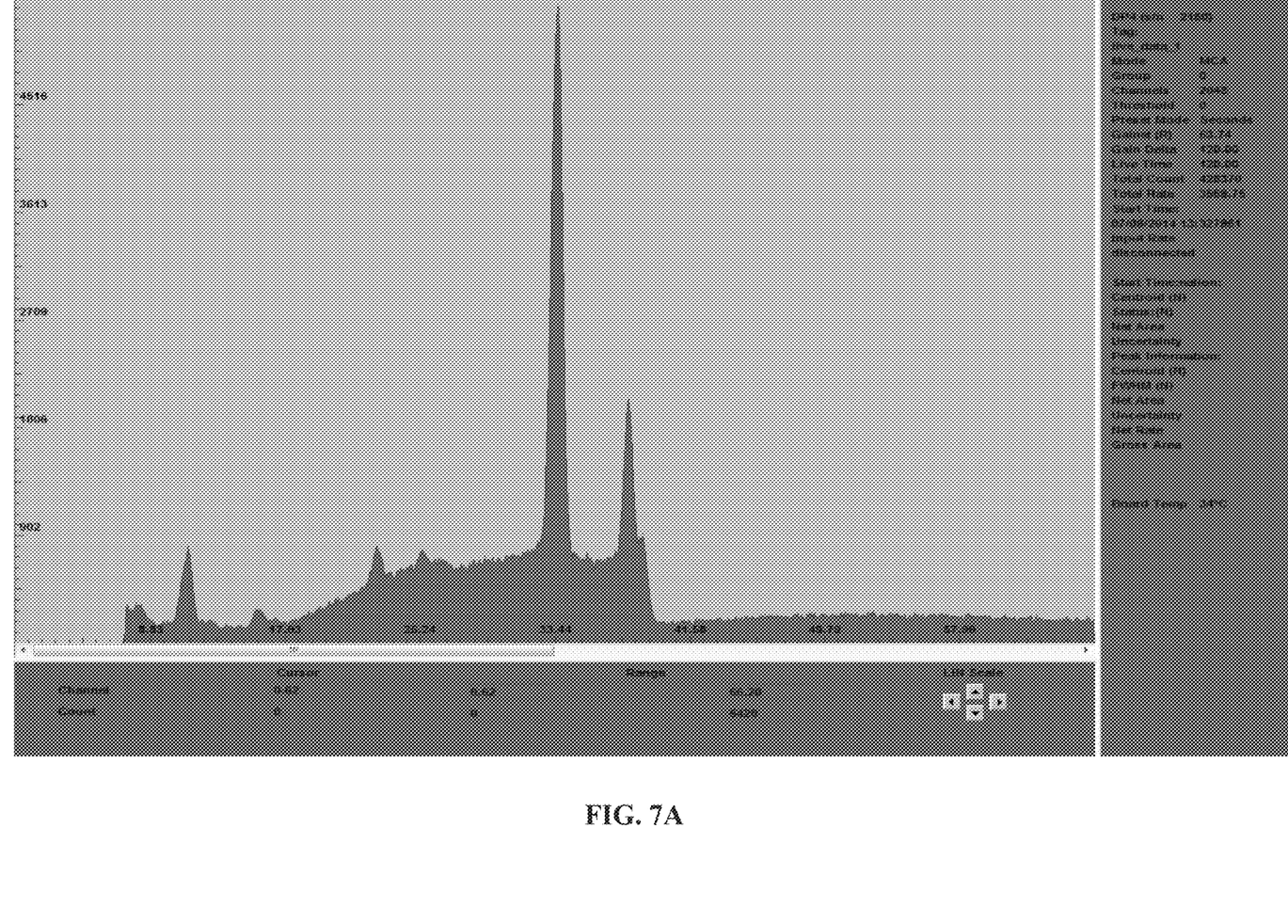
FIGS. 7a and 7b show the emission spectrum of Sb (FIG. 7a) to induce Augers from silver sensor (FIG. 7b) with ~15 Augers from each an inner shell ionization at 12-18 eV each.
Figure 7B:
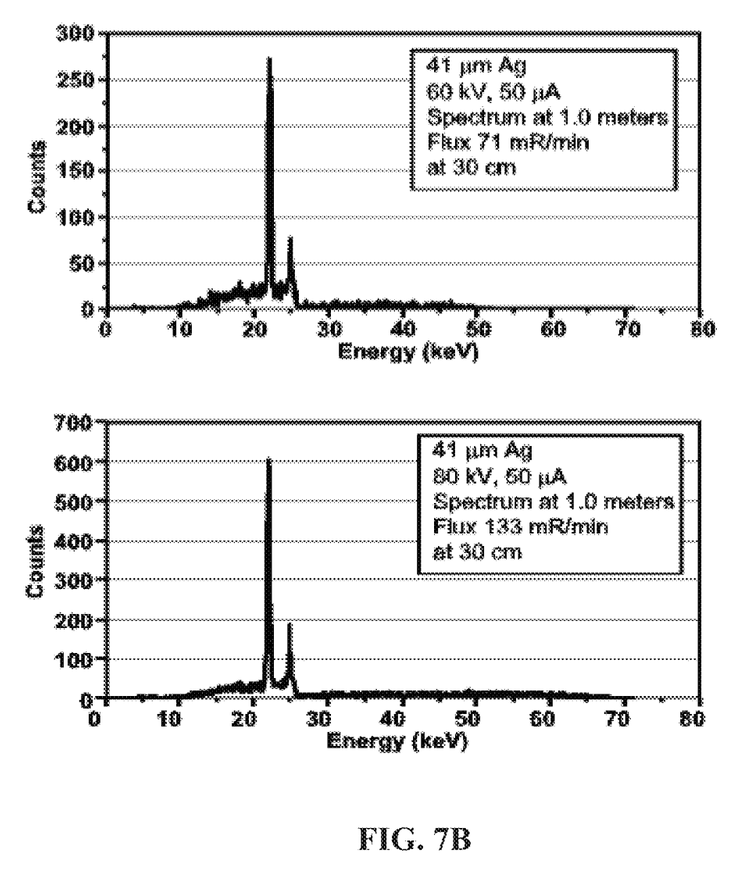
Figure 8:
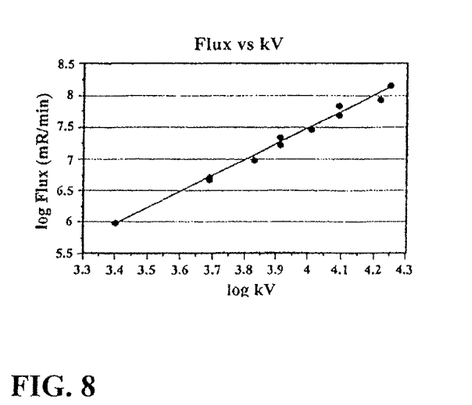
FIG. 8 shows transmission tube brightness, mostly in line-emissions, and how it increases with the tube bias kVp and follows the voltage relationship of $(kVp)^{21}$ due to the relativistic transform while the Coolidge tube harvesting the beam at 90° increases to $(kVp)^{17}$, and the synchrotron radiation decreases to the fourth power of the photon energy and is limited to under approximately 15 keV for most national facilities.

As shown in FIG. 7 for Ag, the change of bias (kVp) will not alter the characteristic line position of Ag, as a result, the high voltage power supply (HVPS) can have a range of voltage windows and thereby greatly simplifies the HVPS design by simple discharge of capacitors, thus reducing the size of HVPS from that of a refrigerator to a couple of shoeboxes.

Compact Auger Mammography without Bucky Grid

We have described an Auger mammography using

Sharp Auger imaging sensor array at 0.1 µm each

PSC imager at 15 cm×10 cm that can selectively display bundled imaging point of 50 µm and zoom for detailed points of interest as sharp as 10 µm for single cells that could distinguish the cyst from tubular growth or neovasculature, for example.

Size of the mammography instrument could be reduced from the size of a refrigerator to a pair of shoe boxes and without the need of breast compression Dose of mammography is reduced to less than 1% from current practice and could serve women of all ages everywhere.

The highly portable unit could be powered by any automobile for universal mobile service.

Using Auger sensor array, the low cost optical CMOS imager with relatively large pixels could readily be modified for Auger imager.

The sharp Auger sensor array at 0.1 µm each allows the monochromatic line X-ray photons to register the PSC imaging. In addition, each imaging pixel sensor could be coated with multiple Auger sensors with each corresponding only to their respective photon energy window and could be excited sequentially from the same focus apparatus and deliver the X-ray beams from the same focal spot of the layered transmission X-ray target under a varied tube biases for target/sensor pair selection. As a result, a simple software routine could manipulate to view the tissues with a range of beam energies from the same setup. The said high energy PSC using Auger imager could also incorporate the viewing of Gd-enhanced neovasculature as well as the Auger-based MegaGy radiation dose in Situ for therapeutic applications.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the following claims.

What is claimed is:

1. An apparatus for examining tissue of a patient for abnormalities, the apparatus comprising:
   (1) a monochromatic X-ray beam generator that emits at least a first beam of monochromatic line emission X-ray photons having an energy at or nearly above an absorption edge of a first element to induce emission of Auger electrons when the first element is irradiated with the X-ray photons; and
   (2) an X-ray detector comprising
      (a) a pixel or plurality of pixels comprising (i) an array of pixel sensors each of which comprises the first element such that the line emission X-ray photons, when received by the pixel sensors in the array, cause a cascade of Auger electrons that form a transient electric charge, and (ii) a semiconductor collection layer configured for receiving the Auger electrons of said transient electric charge; and
      (b) processing electronics for converting the Auger electrons received in the collection layer into a direct radiographic signal;
   wherein X-ray photons in the first beam of monochromatic line emission X-ray photons undergo a spatial and temporal dispersion when passing through soft tissues with density variation so as to cause a density-based phase shift in the X-ray photons, wherein the pixel sensors in the array are of a size and number that enable the pixel sensors to register a phase shift contrast (PSC) image from the radiographic signal from which abnormalities in the tissues are identifiable, wherein the respective pixel sensors in the array are unconnected to each other electrically, and wherein the first element comprises cesium iodide (CsI).

2. The apparatus according to claim 1, wherein the monochromatic X-ray beam generator comprises an end window X-ray tube having an evacuated housing that is sealed from the ambient, an end window anode disposed in the housing comprising a transmission target layer, a cathode disposed in the housing which emits an electron beam that proceeds along a beam path in said housing to strike the anode in a spot so as to generate the first beam of monochromatic X-rays which exits the housing through the end window.

3. The apparatus according to claim 2, wherein the transmission target layer comprises La.

4. The apparatus according to claim 1, further comprising a high voltage power supply.

5. The apparatus according to claim 1, wherein the pixel sensors in the array of pixel sensors are between 0.1 and 0.2μ in size.

6. The apparatus according to claim 1, wherein the processing electronics are covered by a layer of a heavy element to protect the electronics from the X-ray photons.

7. The apparatus according to claim 6, wherein the heavy element comprises Ba or Ta.

8. The apparatus according to claim 1, wherein the array of pixels is on an imager panel of a first semiconductor chip and the processing electronics are disposed at an edge of the imager panel or on a second semiconductor chip that is stacked beneath the first semiconductor chip to shield the second semiconductor chip from radiation.

9. A method for examining breast tissue of a subject for abnormalities, the method comprising the steps of
    (a) providing the apparatus according to claim 1;
    (b) emitting from the monochromatic X-ray beam generator at least the first beam of monochromatic line emission X-ray photons so that the X-ray photons are transmitted through the breast tissue and detected by the detector; and
    (c) causing the detector to generate a radiographic image that reflects a phase shift in the X-ray photons caused by an abnormality in the breast tissue.

10. The method according to claim 9, wherein the monochromatic X-ray beam generator comprises an end window X-ray tube having an evacuated housing that is sealed from the ambient, an end window anode disposed in the housing comprising a transmission target layer, a cathode disposed in the housing which emits an electron beam that proceeds along a beam path in said housing to strike the anode in a spot so as to generate the first beam of monochromatic X-rays which exits the housing through the end window.

11. The method according to claim 10, wherein the examination of the breast tissue is conducted in a manner that enables ≥50% of penetrating X-rays of the first beam to reach the detector after passing through the breast tissue.

12. The method according to claim 11, wherein the examination is carried out with an X-ray photon energy of 25 to 35 keV.

13. The method according to claim 12, wherein, with the end window of the tube disposed within about 10 to 15 cm of a breast of the subject and with the first beam focused under 40μ, a brightness of the end window X-ray tube is adjustable to enable the end window X-ray tube to operate at a thermal load of 100-150 watts for the examination.

* * * * *